US011316560B1

(12) United States Patent
Kerselaers (10) Patent No.: US 11,316,560 B1
(45) Date of Patent: Apr. 26, 2022

(54) MAGNETIC INDUCTION DEVICE

(71) Applicant: NXP B.V., Eindhoven (NL)

(72) Inventor: Anthony Kerselaers, Herselt (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 17/078,475

(22) Filed: Oct. 23, 2020

(51) Int. Cl.
*H04B 5/00* (2006.01)
*A61N 2/02* (2006.01)

(52) U.S. Cl.
CPC .............. *H04B 5/0081* (2013.01); *A61N 2/02* (2013.01); *H04B 5/0031* (2013.01)

(58) Field of Classification Search
CPC .................... A61N 2/00–12; H04B 5/00–02
See application file for complete search history.

(56) References Cited

U.S. PATENT DOCUMENTS

| | | | | |
|---|---|---|---|---|
| 4,524,079 A * | 6/1985 | Hofmann | ............... | A23L 3/01 426/234 |
| 4,654,641 A | 3/1987 | Ferguson et al. | | |
| 5,139,684 A | 8/1992 | Kaali et al. | | |
| 5,185,086 A | 2/1993 | Kaali et al. | | |
| 5,188,738 A | 2/1993 | Kaali et al. | | |
| 7,165,451 B1 * | 1/2007 | Brooks | ............... | A61B 8/00 73/579 |
| 7,280,874 B2 * | 10/2007 | Boehm | ............... | C12N 13/00 435/6.12 |
| 2003/0008287 A1 * | 1/2003 | Black | ............... | G06T 7/0012 435/6.14 |
| 2005/0080459 A1 * | 4/2005 | Jacobson | ............... | A61N 2/02 607/9 |
| 2005/0095197 A1 * | 5/2005 | Tuszynski | ............... | A61K 47/593 424/1.11 |
| 2005/0179511 A1 * | 8/2005 | Bush | ............... | H01F 13/00 335/296 |
| 2007/0179576 A1 * | 8/2007 | Nagano | ............... | A61N 1/406 607/96 |
| 2008/0119421 A1 * | 5/2008 | Tuszynski | ............... | A61K 41/0004 514/34 |

(Continued)

FOREIGN PATENT DOCUMENTS

EP 2067501 A2 6/2009
EP 2067501 A3 6/2009

(Continued)

OTHER PUBLICATIONS

DNA Pathogen Frequencies; "About the Frequency Method"; retrieved from the Internet https://www.dnafrequencies.com/about; 2 pages (Oct. 2020).

*Primary Examiner* — Gennadiy Tsvey (57) ABSTRACT

One example discloses a magnetic induction device, including: a transmitter configured to induce a magnetic signal in a structure; wherein the structure is coupled to a sub-structure; a controller configured to characterize the structure so as to identify a first frequency range of the magnetic signal that resonates with the structure; wherein the controller is configured to identify a second frequency range that resonates with the sub-structure; wherein the controller is configured to select a frequency for the magnetic signal within the first frequency range that has a harmonic frequency in the second frequency range; and wherein the transmitter is configured to transmit the magnetic signal into the structure at the selected frequency.

21 Claims, 6 Drawing Sheets

(56) References Cited

U.S. PATENT DOCUMENTS

| | | | |
|---|---|---|---|
| 2009/0137473 A1* | 5/2009 | Martin | C07K 14/47 514/4.8 |
| 2010/0049261 A1* | 2/2010 | Bare | A61N 1/40 607/1 |
| 2013/0165734 A1* | 6/2013 | Butters | G01N 37/005 600/13 |
| 2016/0256704 A1* | 9/2016 | Petty | A61N 2/004 |
| 2016/0361385 A1* | 12/2016 | Tuszynski | C07K 14/47 |
| 2017/0072210 A1 | 3/2017 | Gangwish et al. | |
| 2019/0111136 A1* | 4/2019 | Liang | A61K 9/0009 |
| 2019/0204376 A1* | 7/2019 | Goyal | G01R 31/2812 |
| 2019/0222066 A1* | 7/2019 | Kozakai | H02J 50/80 |
| 2020/0254272 A1* | 8/2020 | Sharma | A61N 2/004 |
| 2020/0330782 A1* | 10/2020 | Zabara | A61N 2/02 |

FOREIGN PATENT DOCUMENTS

| | | |
|---|---|---|
| EP | 3355481 A1 | 8/2018 |
| KR | 10-2020-0050676 A | 5/2020 |
| WO | WO-2016/000075 A1 | 1/2016 |

\* cited by examiner

MAGNETIC INDUCTION DEVICE

The present specification relates to systems, methods, apparatuses, devices, articles of manufacture and instructions for multi-frequency magnetic induction.

SUMMARY

According to an example embodiment, a magnetic induction device, comprising: a transmitter configured to induce a magnetic signal in a structure; wherein the structure is coupled to a sub-structure; a controller configured to characterize the structure so as to identify a first frequency range of the magnetic signal that resonates with the structure; wherein the controller is configured to identify a second frequency range that resonates with the sub-structure; wherein the controller is configured to select a frequency for the magnetic signal within the first frequency range that has a harmonic frequency in the second frequency range; and wherein the transmitter is configured to transmit the magnetic signal into the structure at the selected frequency.

In another example embodiment, the magnetic signal is a wide-band signal having a center frequency that is in the first frequency range, and having harmonic frequencies that are in the second frequency range.

In another example embodiment, the center frequency has a wavelength ¼ of a longest physical dimension of the structure.

In another example embodiment, the first frequency range resonates with all of the structure; and the second frequency range resonates with all of the sub-structure.

In another example embodiment, the controller is configured to identify the second frequency range using a lookup table stored in a memory.

In another example embodiment, further comprising a receiver configured to detect currents induced within either the structure or sub-structure by the magnetic signal; wherein the controller is configured to sweep the magnetic signal through a set of frequencies and identify the second frequency range based on the detected currents induced in the structure or sub-structure.

In another example embodiment, further comprising a receiver configured to detect currents induced within either the structure or sub-structure by the magnetic signal; wherein the controller is configured to adjust the transmitter in response to the detected currents induced in the structure or sub-structure.

In another example embodiment, the controller is configured to adjust the transmitter to maximize the detected currents induced in the structure or sub-structure.

In another example embodiment, the controller is configured to select a waveform for the magnetic signal that generates the harmonic frequency.

In another example embodiment, the waveform is a square wave or a saw-tooth wave.

In another example embodiment, the waveform is generated by mixing at least two different frequency tones.

In another example embodiment, the transmitter is not in galvanic contact with either the structure or sub-structure.

In another example embodiment, the transmitter is configured to be positioned proximate to the structure but at a location different from a position of the sub-structure.

In another example embodiment, the transmitter corresponds to a magnetic antenna in at least one of: an NFC antenna, an NFMI antenna, or an NFEMI antenna.

In another example embodiment, the structure is a living body; and the sub-structure is at least one of: DNA, bacteria, virus, parasite, fungus, a body appendage, or a body organ.

In another example embodiment, the structure is a living body; the sub-structure is entrained in a fluid; and the fluid is at least one of: blood, lymphatic, synovial, an infection, or urea.

In another example embodiment, the sub-structure is a therapeutic drug activated by the magnetic signal.

In another example embodiment, the sub-structure is an energy radiating bio-marker element powered by the magnetic signal.

In another example embodiment, the structure is an electronic device; and the sub-structure is a fusible link.

In another example embodiment, the structure is a surface; and the sub-structure is an object on the surface.

In another example embodiment, the device is integrated with or embedded in at least one of: a wearable, a smartwatch, an earbud, a pacemaker, a medical belt, or a smartphone.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Research has shown that some bacteria, virus, parasites and fungus entrained in blood or other body fluids or other synthetic fluids can be altered and/or reduced with electric currents.

To provide a therapeutic effect on a patient, some approaches use direct galvanic systems that apply electrical currents by means of electrodes placed into the fluid. The fluid is first extracted from the human or animal or system and then treated in a separated isolated device by applying electrical currents generated by electrical contacts positioned in the fluid.

Other approaches provide a non-invasive biological conditioning device, including inductive structures wherein the structures are configured to induce an electrical current in materials and/or liquids and wherein the electrical current is configured to have a set of attributes for conditioning biological activity in the material and/or liquid. While this method does not require electrodes to be submerged in a biological material for example, it needs to be accurately positioned above the biological material to be targeted.

These protocols require generation of specific frequencies that correspond directly to the specific dimensions of a virus, bacteria, etc. being targeted.

In many cases since the dimensions of a virus, bacteria, etc. are very small, so very high frequencies need to be generated and directly transmitted into a body structure so as to create a therapeutic effect.

Devices for generating these frequencies also need to be positioned directly over a particular body structure to have an effect.

Now discussed is a magnetic induction device for current induction in plurality of structures and sub-structures within the structure (e.g. a body, a fluid, a material, objects on a surface, electronic devices, etc.) wherein not only can lower transmitted frequencies be used, but also due to the resonance characteristics of the structure at the selected transmitted frequencies, the transmitter does not need to be positioned near a particular sub-structure being targeted for current induction within the structure. In many example embodiments, the magnetic induction device can be placed anywhere on the structure and still induce currents in selected sub-structures.

This is possible since the magnetic induction device generates a wide-band magnetic signal having a center frequency that is resonant with the structure and harmonics that are resonant with the sub-structure or sub-structures being targeted for current induction. Such magnetic signal can be generated either by a dedicated inductive coil or by repurposed magnetic antennas (e.g. coils) in devices such as an NFC (Near Field Communication) device, an NFMI (Near Field Magnetic Induction) device, or an NFEMI (Near Field Electromagnetic Induction) device.

Figure 1:
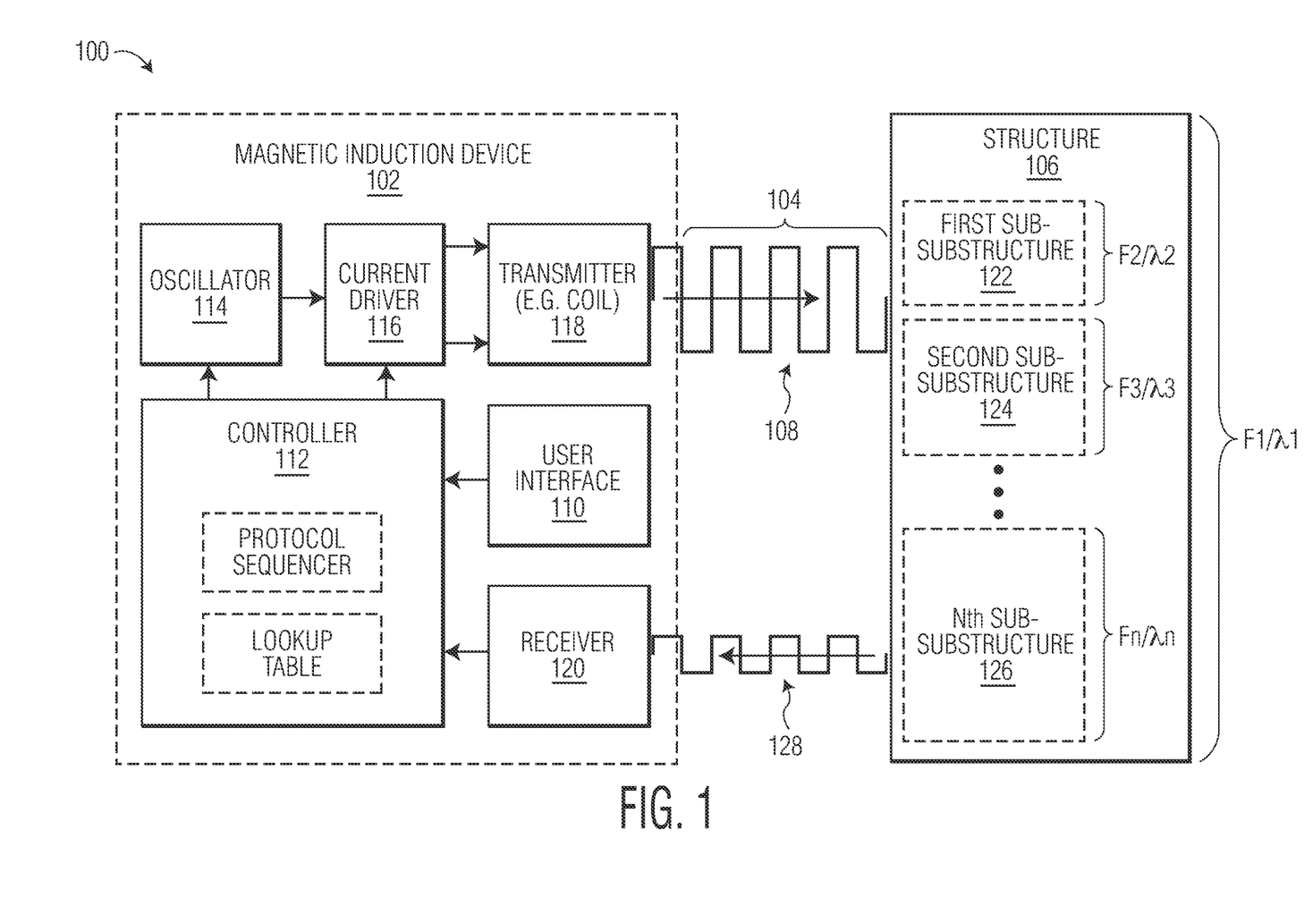
FIG. 1 is an example magnetic induction device.

FIG. 1 is an example 100 magnetic induction device 102. The magnetic induction device 102 is separated by a distance 104 from a structure 106 resonant at $F1/\lambda 1$ (i.e. frequency F1 having a wavelength $\lambda$).

The magnetic induction device 102 is configured to transmit a magnetic signal 108 to the structure 106. The magnetic signal 108 is a wide-band signal that includes a center frequency and a set of harmonics.

The magnetic induction device 102 includes a user interface 110, a controller 112, an oscillator 114, a current driver 116, a transmitter 118 (e.g. coil, applicator, etc.), and a receiver 120 (e.g. magnetic sensor). The a controller 112 includes a protocol sequencer and a lookup table.

The structure 106 includes a set of sub-structures labeled as a first sub-structure 122 resonant at $F2/\lambda$, a second sub-structure 124 resonant at $F3/\lambda 3$, up to an nth sub-structure 126 resonant at $Fn/\lambda n$.

The user interface 110 in some example embodiments enables a user (e.g. doctor, patient, technician, etc.) to select device mode. Device modes can specify therapeutic or non-therapeutic operational modes that target one or more living sub-structures 122, 124, 126 within the structure 106 (either living or non-living). Device modes can also specify operational modes that target one or more non-living sub-structures 122, 124, 126 within the structure 106 (either living or non-living).

In some example embodiments, the device mode targets living sub-structures 122, 124, 126 such as: DNA, bacteria, virus, tumors, parasites, fungus, etc. within a living organism or perhaps bio-reactive sub-structures on a non-living surface to be decontaminated.

In other example embodiments, the device mode targets non-living sub-structures 122, 124, 126 such as: electrical components, fusible-links in a device to be configured, a therapeutic drug (or chemical) traveling through a living body to be activated by the magnetic signal, an energy radiating bio-marker element powered by the magnetic signal (e.g. radio-nucleotide for detection of aggregation sites for a targeted tumor or pathogen within a living body), or a consumer item structure including a security sub-structure to be deactivated after purchase.

In response to the device mode selected by the user interface 110, the controller 112 is configured to select a protocol corresponding to the device mode. The protocol in various example embodiments includes a set of frequencies, waveforms and durations for the magnetic signal 108 to be transmitted into the structure 106.

The controller 112 is configured to characterize the structure 106 so as to identify a first frequency range of the magnetic signal 108 that resonates with the structure 106 (i.e. including $F1/\lambda 1$). The controller 112 is then configured to identify a second frequency range that resonates with one or more of the sub-structures 122, 124, 126 (i.e. including $F2/\lambda 2$, $F3/\lambda$, $Fn/\lambda n$). These characterizations can be implemented either passively using the lookup table in the controller 112 or actively by sweeping the magnetic signal 108 and using the receiver 120 to detect a monitoring signal 128 corresponding to the currents induced within the structure 106 and/or sub-structures 122, 124, 126 by the magnetic signal 108.

The protocol sequencer in the controller 112 then selects a frequency for the magnetic signal 108 within the first frequency range that has a harmonic in the second frequency range. The protocol sequencer also selects a set of waveforms and durations (e.g. a signal signature) corresponding to the device mode and targeted sub-structures 122, 124, 126.

In some example embodiments the harmonic frequency has a wavelength equal to the targeted sub-structure 122, 124, or 126 in the structure 106 (e.g. bacteria in a body structure). However in other example embodiments the harmonic frequency has a wavelength greater than or less than the targeted sub-structure in the structure 106 as long as a desired therapeutic and/or device effect is achieved.

In some example embodiments the magnetic signal 108 can have a 1 kHz to 100 MHz center frequency for an untuned coil and if the magnetic signal 108 is a square-wave or saw-tooth-wave the harmonics can go up to 1 GHz.

The controller 112 is coupled to the oscillator 114 and current driver 116 which then create a signal signature according to the protocol selected by the sequencer. The oscillator 114 generates the protocol waveforms and the current driver 116 drives the magnetic transmitter 118 in a single-ended or balanced way for the durations specified by the sequencer.

The magnetic transmitter 118 then converts the drive currents into the magnetic signal 108 transmitted into the structure 106. The magnetic transmitter 118 (e.g. coil) is positioned at about the distance 104 from the structure 106. However since the magnetic signal 108 is resonant with an entirety of the structure 106 (e.g. head-to-toe) the transmitter 118 can be positioned at any convenient location near the structure 106.

The device 102 in some example embodiments includes a rechargeable battery (not shown) so that the device 102 can be used as a wearable for example.

Figure 2A:
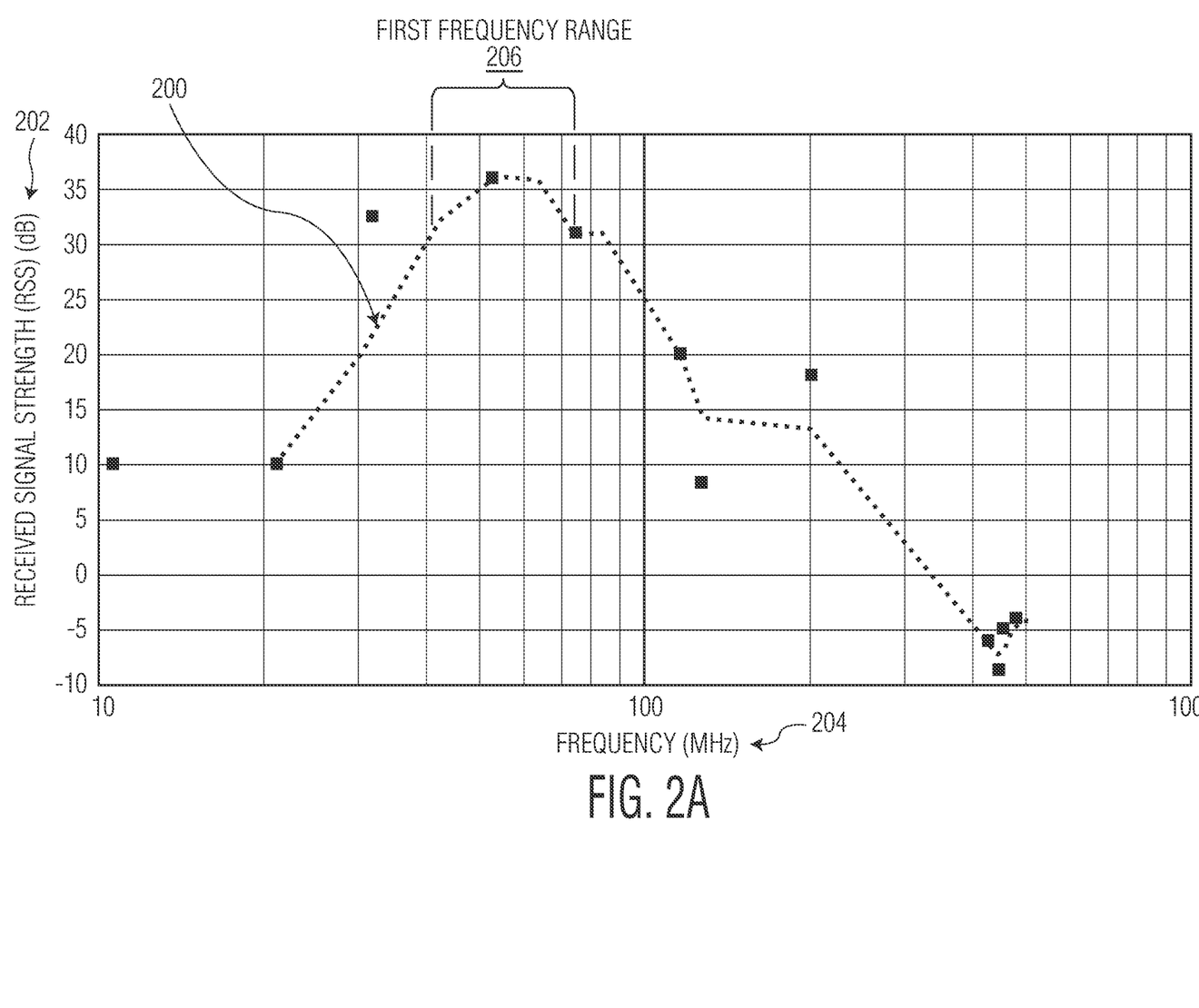
FIG. 2A is an example energy resonance profile for a structure.

FIG. 2A is an example current resonance profile 200 for the structure 106. In this particular example 200 the structure 106 is a standing human body and the sub-structure 122, 124, or 126 (discussed in FIG. 2B) will be a theoretical portion of the human body structure.

The received signal strength (RSS) (dB) 202 corresponds to a relative amplitude of currents induced in the body structure 106 in response to the magnetic signal 108 over a set of frequencies (MHz) 204.

A strongest current resonance band of the structure 106 corresponding to the −3 dB points (i.e. ½ power) of the RSS signal 204 is defined as a first frequency range 206, which in this example is between about 40 MHz and 80 MHz. As discussed above the controller 112 identified the first frequency range 206 which would include F1/λ1.

The first frequency range 206 corresponds to an aggregation of currents from various conductive sub-structures 122, 124, 126 within the structure 106 depending on their dimensions and proximity to a ground plane (i.e. ground on which the body is standing in this example 200).

A longest-dimension (i.e. length) of the body can be considered as a quarter wavelength (¼ λ1) monopole antenna with the ground as reference plane. Induced currents substantially within the first frequency range 206 will generate currents along the length of the body due to the quarter wave antenna effect or resonance effect. This is why the transmitter 118 does not need to be positioned very accurately to generate enough current density to act on the targeted biological or sub-structure(s) 122, 124, and/or 126.

Figure 2B:
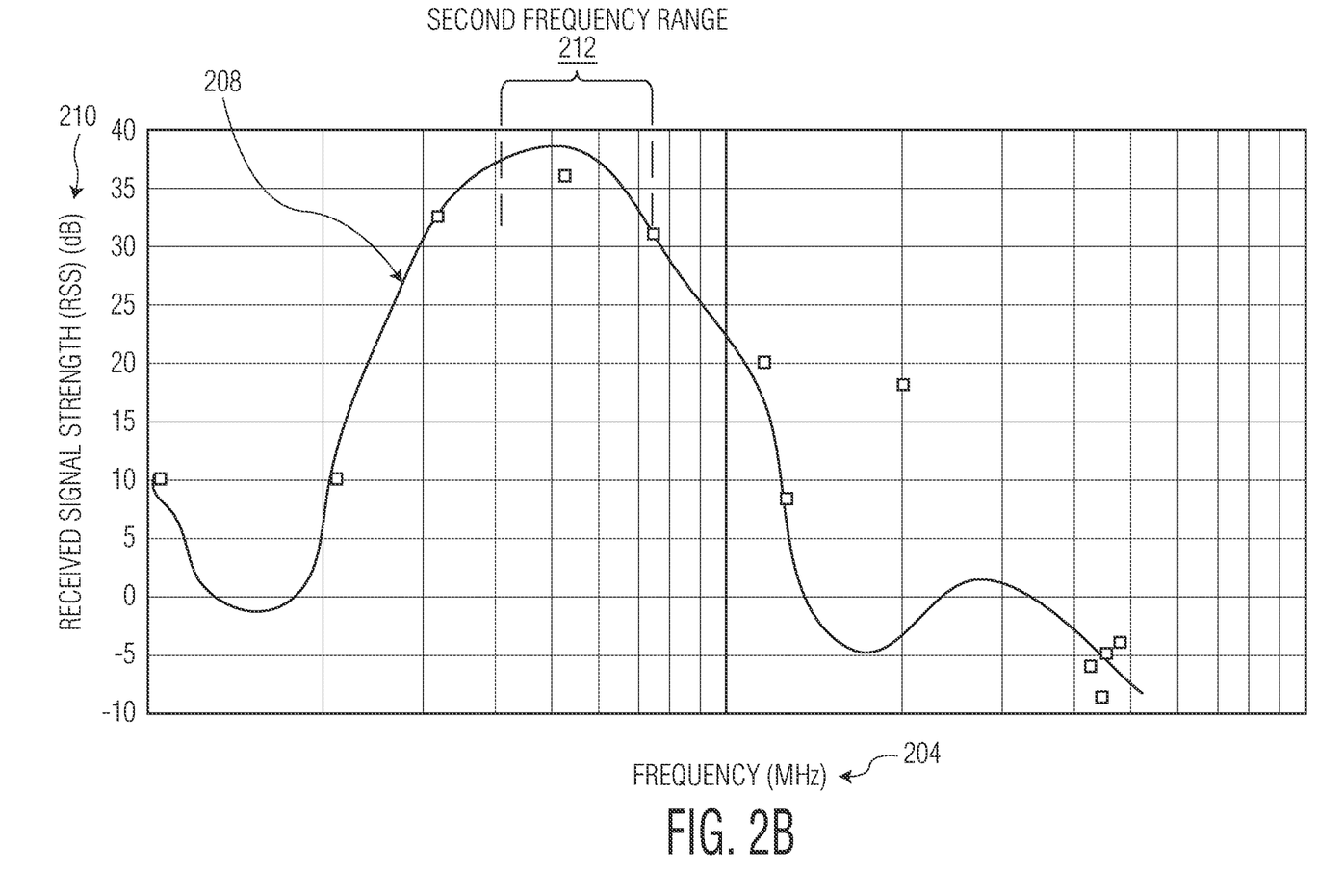
FIG. 2B is an example energy resonance profile for a sub-structure within the structure.

FIG. 2B is an example energy resonance profile 208 for one or more sub-structures 122, 124, and/or 126 within the structure 106.

The received signal strength (RSS) (dB) 210 corresponds to a relative amplitude of currents induced in the sub-structure(s) 122, 124, and/or 126 in response to the magnetic signal 108. Since the sub-structure(s) 122, 124, and/or 126 have differing dimensions than the structure 106, the set of frequencies (MHz) 204 are centered about one or more harmonics of the center frequency of the magnetic signal 108.

A strongest current resonance band of at least one of the structures 122, 124, and/or 126 corresponding to the −3 dB points (i.e. ½ power) of the RSS signal 210 is defined as a second frequency range 212. As discussed above the controller 112 identified the second frequency range 212 either using the lookup table or the sweeping method and will include F2/λ2, F3/λ3, and/or Fn/λn.

In various example embodiments, an amplitude of the induced currents generated by the magnetic signal 108 will depend upon where the transmitter 118 is placed near the structure 106, but the first frequency range 208 and the second frequency range 212 will still be the same.

Figure 3:
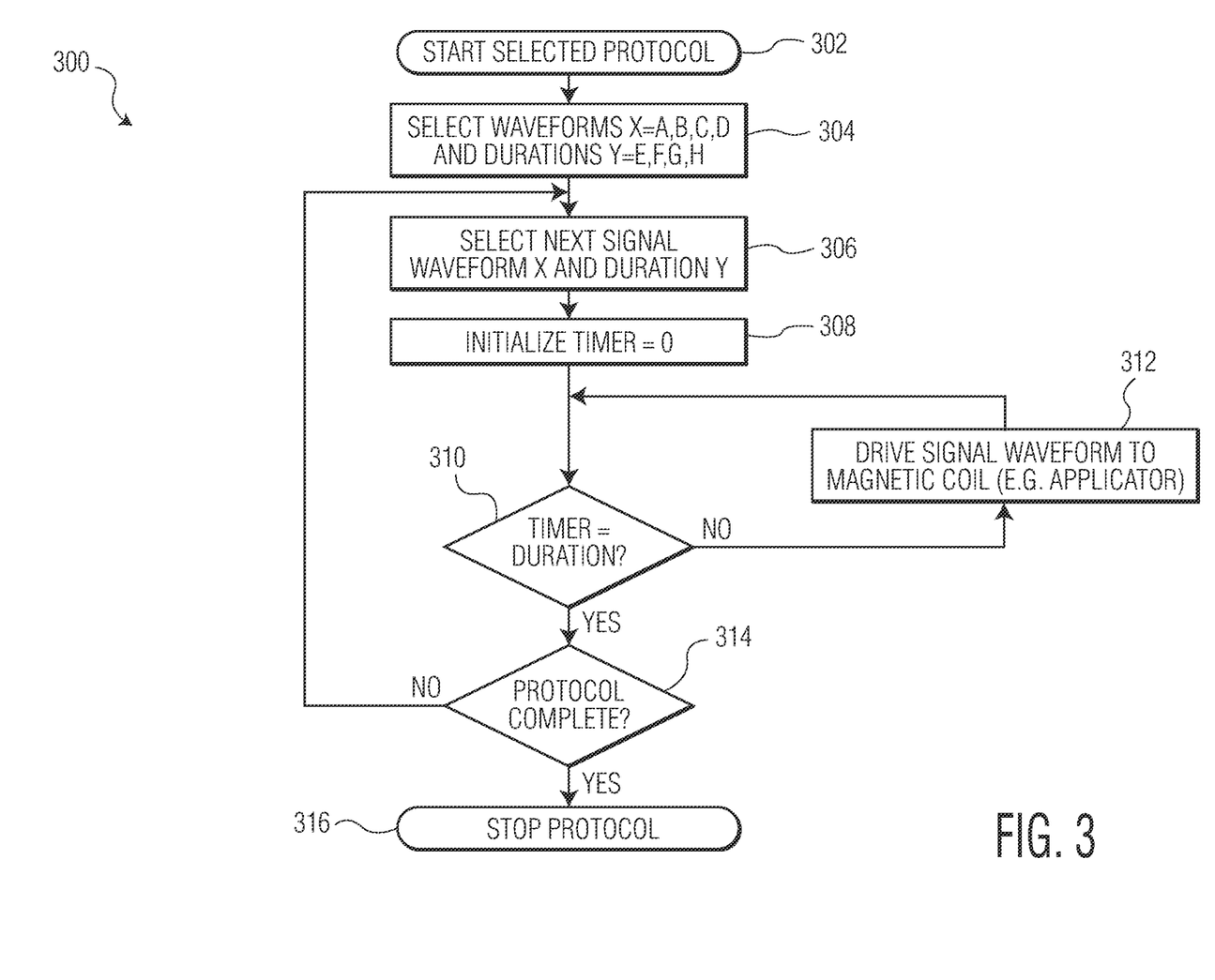
FIG. 3 is an example set of instructions for controlling the magnetic induction device.

FIG. 3 is an example set of instructions 300 for controlling the magnetic induction device. In this example the instructions 300 correspond to one or more protocols discussed above.

In step 302 start selected protocol. In step 304 select a sequence of waveforms X=A, B, C, D and corresponding durations Y=E, F, G, H for the magnetic signal 108. In step 306 select next signal waveform X and duration Y. In step 308 initialize timer=0. In step 310 "Timer=Duration?". If no, then in step 312 drive signal waveform to magnetic transmitter 118. If yes, then in step 314 "Protocol complete?". If no, then return to step 306. If yes, then in step 316 stop protocol.

Different signal waveforms are generate each portion of the magnetic signal 108 for a certain time duration corresponding to the protocol sequence's selections. In some example embodiments, the signal waveforms may have a same time-domain waveform but varying frequencies (i.e. repetition rates).

In one specific example protocol, a bidirectional square pulse at 1 kHz frequency and having a fixed time duration is transmitted by the device 102 for 3 minutes. Then for 6 minutes the bidirectional square pulse is transmitted with a 33 kHz frequency. Finally for 10 minutes the bidirectional square pulse is transmitted with a 10 kHz frequency. Such a protocol could be tailored to reduction of overgrowth of a particular bacteria's in particular biological structure.

Waveforms and Durations (e.g. signal signatures) vary depending upon the targeted sub-structure(s) (e.g. DNA, bacteria, virus, objects, pathogens, conditions, etc.)

In some example embodiments the set of instructions described above are implemented as functional and software instructions. In other embodiments, the instructions can be implemented either using logic gates, application specific chips, firmware, as well as other hardware forms.

When the instructions are embodied as a set of executable instructions in a non-transitory computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transitory machine or computer-usable media or mediums as defined herein excludes signals, but such media or mediums may be capable of receiving and processing information from signals and/or other transitory mediums.

Figure 4:
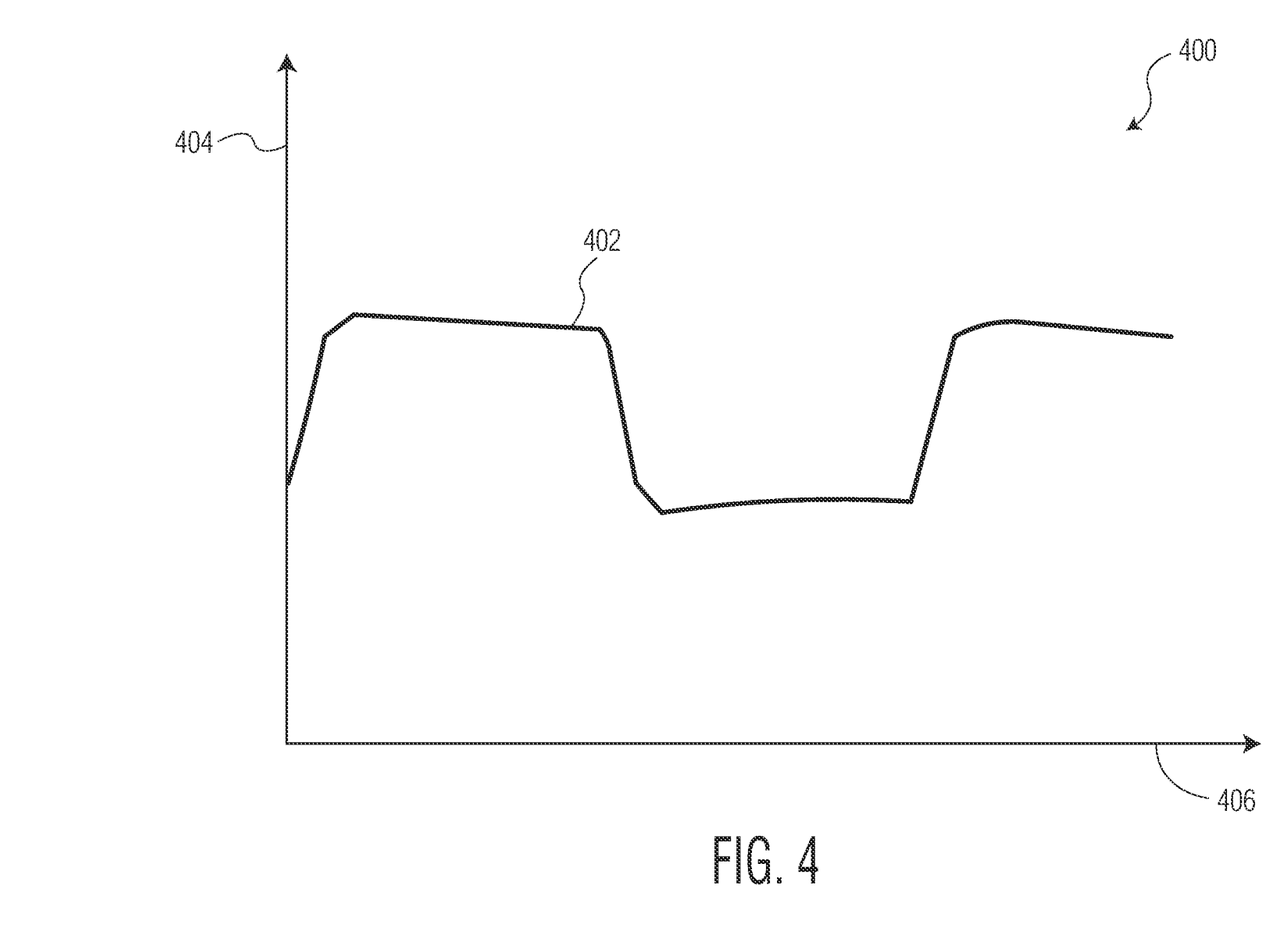
FIG. 4 shows an example current waveform driving a magnetic induction device coil located nearby the structure.

FIG. 4 shows an example 400 current waveform 402 driving the magnetic induction device 102 transmitter 118 located nearby the structure 106. The waveform 402 is within the first frequency range 206 of the structure 106 and in this example 400 is also a square-wave. The square-wave by its nature is a wide-band signal and has many harmonics.

The waveform's 402 current (mA) 404 verses time 406 (4 μsec) is shown as measured by a current probe coupled to the structure 106. In this example 400 the magnetic signal 108 waveform 402 is a square-wave (i.e. wideband) signal having a peak current amplitude is 120 mA over the 4 μsec time window shown. In other example embodiments the the magnetic signal 108 waveform could be a saw-tooth-wave or any other wide-band signal having at least one harmonic.

Figure 5:
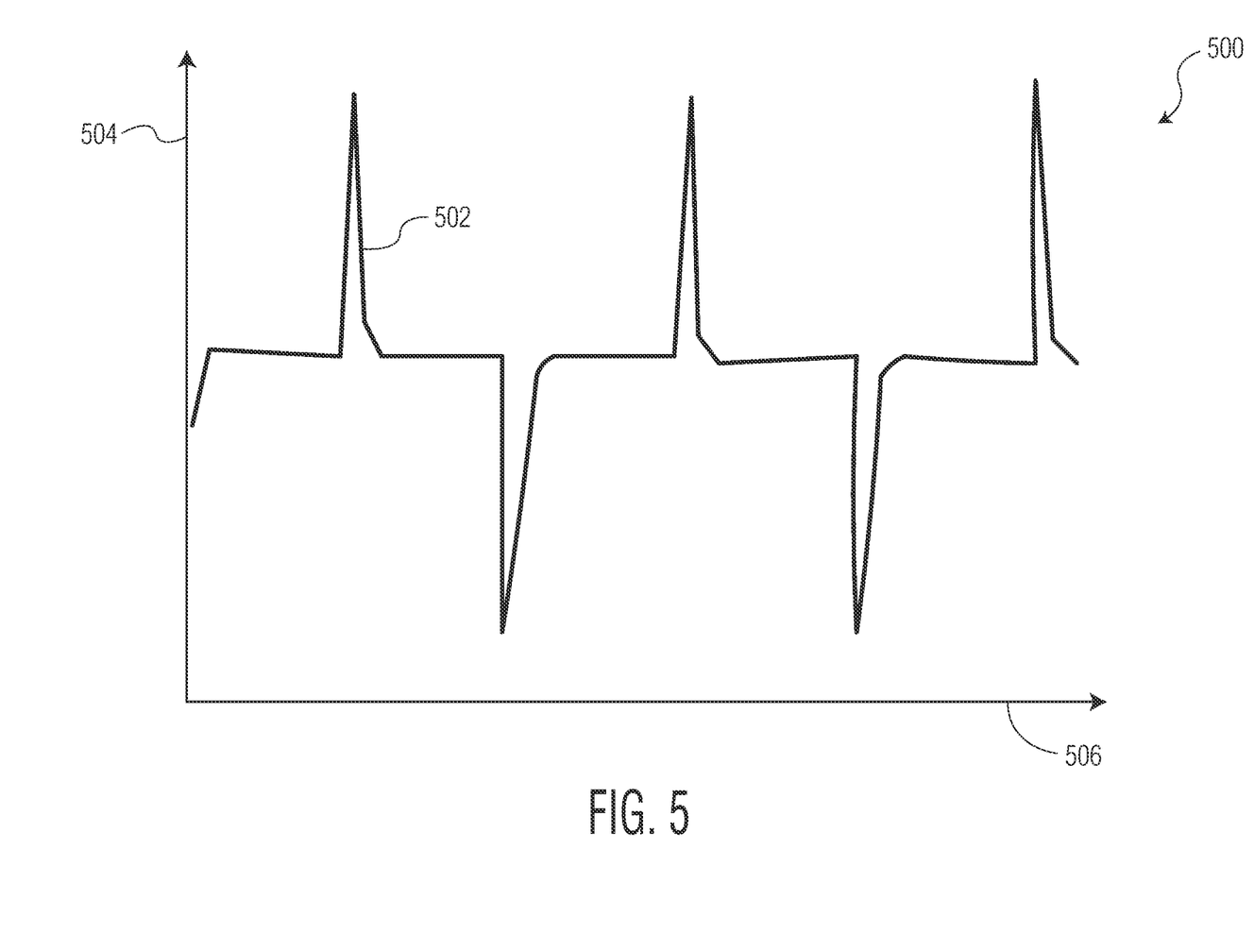
FIG. 5 shows an example current waveform induced in a sub-structure coupled to the structure.

FIG. 5 shows an example 500 current waveform 502 induced in the sub-structure 122, 124, or 126 coupled to the structure 106. This particular example 500 is generated in response to the magnetic signal 108 waveform 402 transmitted into the structure 106 discussed in FIG. 4.

The waveform's 502 current 504 verses time 506 is shown. In this example embodiment, the current waveform 502 corresponds to an induced current density of about 84 uA/cm$^2$. The induced current waveform 502 in this example 500 is at a higher frequency than the current waveform 402 driving the transmitter 118, and is associated with therapeutic medical effects in the human body structure.

The current waveform 402 is within the first frequency range 206 and thus is resonant with the structure 106 (i.e.

human body). Since the current waveform 402 is resonant over the structure 106 the induced current waveform 502 within the second frequency range 212 is distributed across the complete human body structure thus having a therapeutic medical effect over the complete human body.

The various device 102 example embodiments discussed above may be integrated with or embedded in devices such as: a wearable, a smartwatch, an earbud, a pacemaker, a medical belt, a smartphone, and so on.

In some example embodiments, the device 102 induces currents in biomaterials such as blood of a human or animal that are sufficient to have an effect on (e.g. decrease the activity of) bacteria, virus, parasites and fungus entrained in the blood or other body fluids or other synthetic fluids. The device 102 can be used to selectively destroy cancer cells or bring damage to them to prevent them from further cell divisions and tumor growth.

In some example applications of the device 102, the induced currents will be strongest in the most conductive portions of the structure 106 (e.g. blood within a human body).

Because of the differentiation in resonance frequencies of different biological structures, the device 102 is selective in its therapeutic or other effect. Certain specific therapeutic effects possible using the device 102 and specific waveforms, frequencies and durations are known to those skilled in the art.

Thus the device 102 opens up a possibility for small, wearable devices with flexible positions on a human body or other structures 106 for various applications.

Example embodiments of the material discussed in this specification can be implemented in whole or in part through network, computer, or data based devices and/or services. These may include cloud, internet, intranet, mobile, desktop, processor, look-up table, microcontroller, consumer equipment, infrastructure, or other enabling devices and services. As may be used herein and in the claims, the following non-exclusive definitions are provided.

In one example, one or more instructions or steps discussed herein are automated. The terms automated or automatically (and like variations thereof) mean controlled operation of an apparatus, system, and/or process using computers and/or mechanical/electrical devices without the necessity of human intervention, observation, effort and/or decision.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A magnetic induction device, comprising:
a transmitter configured to induce a magnetic signal in a structure;
wherein the structure is coupled to a sub-structure;
a controller configured to characterize the structure so as to identify a first frequency range of the magnetic signal that resonates with the structure;
wherein the controller is configured to identify a second frequency range that resonates with the sub-structure;
wherein the controller is configured to select a frequency for the magnetic signal within the first frequency range that has a harmonic frequency in the second frequency range; and
wherein the transmitter is configured to transmit the magnetic signal into the structure at the selected frequency.

2. The device of claim 1:
wherein the magnetic signal is a wide-band signal having a center frequency that is in the first frequency range, and having harmonic frequencies that are in the second frequency range.

3. The device of claim 2:
wherein the center frequency has a wavelength ¼ of a longest physical dimension of the structure.

4. The device of claim 1:
wherein the first frequency range resonates with all of the structure; and
wherein the second frequency range resonates with all of the sub-structure.

5. The device of claim 1:
wherein the controller is configured to identify the second frequency range using a lookup table stored in a memory.

6. The device of claim 1:
further comprising a receiver configured to detect currents induced within either the structure or sub-structure by the magnetic signal;
wherein the controller is configured to sweep the magnetic signal through a set of frequencies and identify the second frequency range based on the detected currents induced in the structure or sub-structure.

7. The device of claim 1:
further comprising a receiver configured to detect currents induced within either the structure or sub-structure by the magnetic signal;
wherein the controller is configured to adjust the transmitter in response to the detected currents induced in the structure or sub-structure.

8. The device of claim 7:
wherein the controller is configured to adjust the transmitter to maximize the detected currents induced in the structure or sub-structure.

9. The device of claim 1:
wherein the controller is configured to select a waveform for the magnetic signal that generates the harmonic frequency.

10. The device of claim 9:
wherein the waveform is a square wave or a saw-tooth wave.

11. The device of claim 9:
wherein the waveform is generated by mixing at least two different frequency tones.

12. The device of claim 1:
wherein the transmitter is not in galvanic contact with either the structure or sub-structure.

13. The device of claim 1:
wherein the transmitter is configured to be positioned proximate to the structure but at a location different from a position of the sub-structure.

14. The device of claim 1:
wherein the transmitter corresponds to a magnetic antenna in at least one of: an NFC antenna, an NFMI antenna, or an NFEMI antenna.

15. The device of claim 1:
wherein the structure is a living body; and
wherein the sub-structure is at least one of: DNA, bacteria, virus, parasite, fungus, a body appendage, or a body organ.

16. The device of claim 1:
wherein the structure is a living body;

wherein the sub-structure is entrained in a fluid; and
wherein the fluid is at least one of: blood, lymphatic, synovial, an infection, or urea.

17. The device of claim 1:
wherein the sub-structure is a therapeutic drug activated by the magnetic signal.

18. The device of claim 1:
wherein the sub-structure is an energy radiating biomarker element powered by the magnetic signal.

19. The device of claim 1:
wherein the structure is an electronic device; and
wherein the sub-structure is a fusible link.

20. The device of claim 1:
wherein the structure is a surface; and
wherein the sub-structure is an object on the surface.

21. The device of claim 1:
wherein the device is integrated with or embedded in at least one of: a wearable, a smartwatch, an earbud, a pacemaker, a medical belt, or a smartphone.

\* \* \* \* \*